United States Patent

Buzzetti et al.

Patent Number: 5,397,787
Date of Patent: Mar. 14, 1995

[54] VINYLENE-AZAINDOLE DERIVATIVES

[75] Inventors: Franco Buzzetti, Milan; Angelo Crugnola, Varese; Dario Ballinari, Milan; Felicita Greco, Brescia, all of Italy

[73] Assignee: Farmitalia Carlo Erba S.R.L., Milan, Italy

[21] Appl. No.: 171,154

[22] Filed: Dec. 22, 1993

[30] Foreign Application Priority Data

Dec. 23, 1992 [GB] United Kingdom ............... 9226855

[51] Int. Cl.$^6$ .................. A61K 31/435; C07D 471/04
[52] U.S. Cl. .................................... 514/300; 546/113
[58] Field of Search ........................ 546/113; 514/300

[56] References Cited

U.S. PATENT DOCUMENTS 5,122,537  6/1992  Buzzetti et al. ............... 514/510
5,130,472  7/1992  Buzzetti et al. ............... 560/252

FOREIGN PATENT DOCUMENTS

WO91/13055  9/1991  WIPO .

*Primary Examiner*—Bernard Dentz
*Attorney, Agent, or Firm*—Oblon, Spivak, McClelland, Maier & Neustadt

[57] ABSTRACT

The present invention relates to the compounds of formula (I)

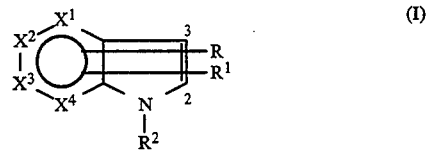

wherein
one of the groups $X^1$ to $X^4$ is N and the others are CH; the rest of the variables are as defined in the specification.

8 Claims, No Drawings

VINYLENE-AZAINDOLE DERIVATIVES

The present invention relates to new vinylene-azaindole derivatives, to a process for their preparation, to pharmaceutical compositions containing them and to their use as therapeutic agents. The present invention provides compounds having the following general formula (I)

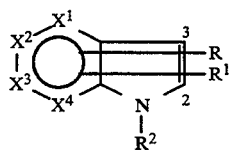

(I)

wherein
one of the groups $X^1$ to $X^4$ is N and the others are CH;
R is a group of formula (a), (b), (c), (d) or (e)

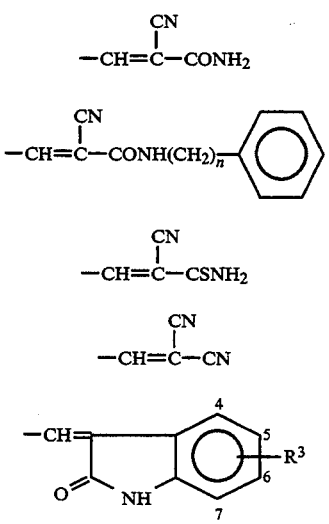

in which
n is zero or an integer of 1 to 5;
$R^1$ is hydrogen, halogen, $C_1$-$C_6$ alkyl, $C_1$-$C_6$ alkoxy, nitro or a group —$NR^4R^5$ wherein each of $R_4$ and $R_5$ is independently hydrogen or $C_1$-$C_6$ alkyl;
$R^2$ is hydrogen, $C_1$-$C_6$ alkyl or $C_1$-$C_6$ alkanoyl;
$R_3$ is hydrogen, halogen, hydroxy, $C_1$-$C_6$ alkoxy, carboxy, nitro or a group —$NR^4R^5$ wherein $R^4$ and $R^5$ are as defined above, and the pharmaceutically acceptable salts thereof.

In the compounds of the invention each of the substituents R and $R^1$ may be independently on either of the pyridine or pyrrole moieties of the bicyclic azaindole ring.

The invention includes within its scope all the possible isomers, stereoisomers, in particular Z- and E-isomers and their mixtures, and the metabolites and the metabolic precursors or bio-precursors (otherwise known as pro-drugs) of the compounds of formula (I). The substituent R is preferably linked to position 2 or 3 of the azaindole ring, in particular to position 3. The substituent $R^1$ is preferably on the pyridine moiety, in particular on the carbon adjacent to the nitrogen ring atom. When one of $R^1$ and $R^3$ is nitro or a —$NR^4R^5$ group as defined above, then the other has preferably a different meaning. The $R^3$ substituent is preferably in 5-position of the oxindole ring (e).

The alkyl groups and the alkyl moiety in the alkoxy and alkanoyl groups may be branched or straight alkyl chain. A $C_1$-$C_6$ alkyl group is preferably a $C_1$-$C_4$ alkyl group, e.g. methyl, ethyl propyl, isopropyl, butyl, sec-butyl or tert-butyl, in particular methyl or ethyl.

A $C_1$-$C_6$ alkoxy group is preferably a $C_1$-$C_3$ alkoxy group, in particular methoxy, ethoxy or n-propoxy.

A $C_2$-$C_6$ alkanoyl group is preferably a $C_2$-$C_3$ alkanoyl group, in particular acetyl or propionyl.

A halogen is preferably fluorine, chlorine or bromine, in particular chlorine.

Pharmaceutically acceptable salts of the compounds of the invention include acid addition salts with inorganic, e.g. nitric, hydrochloric, hydrobromic, sulphuric, perchloric and phosphoric, acids, or organic, e.g. acetic, propionic, glycolic, lactic, oxalic, malonic, malic, maleic, tartaric, citric, benzoic, cinnamic, mandelic and salicylic, acids, and salts with inorganic, e.g. alkali metal, especially sodium or potassium, bases or alkaline-earth metal, especially calcium or magnesium, bases, or with organic bases, e.g. alkylamines, preferably triethylamine.

As stated above, the present invention also includes within its scope pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are the compounds of formula (I), wherein the groups $X^1$ to $X^4$ are as defined above;
R is as defined above and is linked in position 2 or 3 of the azaindole ring;
n is zero;
$R^1$ is hydrogen or a halogen or $C_1$-$C_3$ alkoxy group linked to the carbon atom adjacent to the nitrogen atom in the pyridine moiety;
$R^2$ is hydrogen or $C_1$-$C_4$ alkyl; and, when R is group (e),
$R^3$ is hydrogen or a hydroxy group linked in position 5 of the oxoindole ring, and the pharmaceutically acceptable salts thereof.

More preferred compounds of the invention are the compounds of formula (I) in which the groups $X^1$ to $X^4$ are as defined above;
R is as defined above and is linked in position 3 of the azaindole ring;
n is zero;
$R^1$ and $R^2$ are hydrogen atoms; and, when R is group (e),
$R^3$ is hydrogen or a hydroxy group linked in position 5 of the oxindole ring and the pharmaceutically acceptable salts thereof.

Examples of specific compounds of the invention are the following compounds, which may be either Z- or E-diastereomers or Z,E-mixtures of said diastereomers:
2-cyano-3-(7-azaindol-3-yl)acrylamide;
2-cyano-3-(7-azaindol-3-yl)acrylanilide;
2-cyano-3-(7-azaindol-3-yl)thioacrylamide;
2-cyano-3-(7-azaindol-3-yl)acrylonitrile;
3-[(7-azaindol-3-yl)methylen]-2-oxindole;
5-hydroxy-3-[(7-azaindol-3-yl)methylen]-2-oxindole;
2-cyano-3-(6-azaindol-3-yl)acrylamide;
2-cyano-3-(6-azaindol-3-yl)acrylanilide;

2-cyano-3-(6-azaindol-3-yl)thioacrylamide;
2-cyano-3-(6-azaindol-3-yl)acrylonitrile;
3-[(6-azaindol-3-yl)methylen]-2-oxindole;
5-hydroxy-[(6-azaindol-3-yl)methylen]-2-oxindole;
2-cyano-3-(5-azaindol-3-yl)acrylamide;
2-cyano-3-(5-azaindol-3-yl)acrylanilide;
2-cyano-3-(5-azaindol-3-yl)thioacrylamide;
2-cyano-3-(5-azaindol-3-yl)acrylonitrile;
3-[(5-azaindol-3-yl)methylen]-2-oxindole;
5-hydroxy-3-[5-azaindol-3-yl]-2-oxindole;
2-cyano-3-(4-azaindol-3-yl)acrylamide;
2-cyano-3-(4-azaindol-3-yl)acrylanilide;
2-cyano-3-(4-azaindol-3-yl)thioacrylamide;
2-cyano-3-(4-azaindol-3-yl)acrylonitrile;
3-[(4-azaindol-3-yl)methylen]-2-oxindole;
5-hydroxy-3-[(4-azaindol-3-yl)methylen]-2-oxindole;
and, if the case, the pharmaceutically acceptable salts thereof.

The compounds of the invention, and the pharmaceutically acceptable salts thereof, can be obtained by a process comprising the condensation of an aldehyde of formula (II)

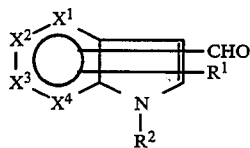

wherein the groups $X^1$ to $X^4$ $R^1$ and $R^2$ are as defined above, with a compound of formula (a'), (b'), (c'), (d') or (e'), respectively:

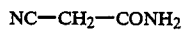 (a')

 (b')

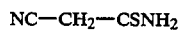 (c')

 (d')

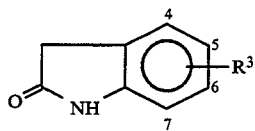 (e)

wherein $R^3$ and n are as defined above, and, if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of a compound of formula (I) into the single isomers.

Each of the substituents $R^1$ and —CHO in a compound of formula (II) may be independently on either of the pyridine or pyrrole moiety of the azaindole ring.

The reaction of a compound of formula (II) with a compound of formula (a'), (b'), (c'), (d') or (e') may be carried out according to known methods, as herebelow described; preferably in the presence of a basic catalyst, e.g. pyridine, piperidine, dimethylamine, or a suitable alkali metal hydroxide or alkoxide.

For example the reaction of a compound of formula (II) with a compound of formula (a'), (b'), (c'), (d') or (e'), respectively, may be carried out under the conditions of the Knoevenagel reactions as described e.g. by Jones in Organic Reactions 15, 204 (1967). Suitable catalysts are organic bases such as pyridine, piperidine or diethylamine.

The condensation may be performed in an inert organic solvent e.g. pyridine, ethanol, methanol, benzene or dioxane at temperatures ranging from about 0° C. to about 100° C.

Preferably the reaction is carried out in warm ethanol solution in the presence of piperidine catalyst. A compound of formula (I) can be converted into another compound of formula (I) according to known methods. For example the de-etherification of a compound of formula (I), wherein $R^1$ and/or $R^3$ is methoxy, so as to obtain a compound of formula (I), wherein $R^1$ and/or $R^3$ is hydroxy, can be carried out for example with boron tribromide as described by J. F. N. McOmie in Tetrahedron 24, 2289 (1968). The reaction may be performed in an inert organic solvent such as dichloromethane, pentane or benzene under an inert, e.g. nitrogen, atmosphere at temperatures ranging from about −78° C. to about room temperature.

The conversion of a compound of formula (I) in which $R^3$ is nitro into the corresponding compound of formula (I) wherein $R^3$ is amino may be carried out following known methods, for example with a variety of reducing agents, e.g. sodium sulfide in hydroalcoholic solution, metallic iron with ammonium chloride in aqueous solvent, or, for instance, catalytic hydrogenations using, e.g., palladium charcoal catalyst at low hydrogen pressure in an inert organic solvent.

The alkylation of a compound of formula (I), wherein $R^2$ is hydrogen, so as to obtain the corresponding compound of formula (I) wherein $R^2$ is a $C_1$–$C_6$ alkyl group, may be obtained, e.g., by reaction with sodium hydride and $C_1$–$C_6$ alkyl iodide in a high boiling aromatic solvent such as xylene.

The acylation of a compound of formula. (I), wherein $R^2$ is hydrogen, in order to obtain the corresponding compound of formula (I) wherein $R^2$ is a $C_2$–$C_6$ alkanoyl, can be performed, e.g. , by reaction with a suitable carboxylic anhydride in the presence of a basic agent at temperatures ranging from room temperature to reflux temperatures.

The alkoxylation of a compound of formula (I) wherein $R^1$ is a halogen adjacent to the pyridine nitrogen, so as to obtain the corresponding compound of formula (I) wherein $R^1$ is $C_1$–$C_6$ alkoxy, may be carried out, e.g., by reaction with a sodium alkoxide in refluxing DMF solution.

The amination of a compound of formula (I) wherein $R^1$ is a halogen adjacent to the pyridine nitrogen, so as to obtain the corresponding compound of formula (I) wherein $R^1$ is a $-NR^4R^5$ group in which one or both of $R^4$ and $R^5$ is $C_1$–$C_6$ alkyl, may be carried out, e.g., by reaction with the corresponding amine of formula $NHR^3R^4$ at reflux temperature.

The optional salification of a compound of formula (I) as well as the conversion of a salt into the free compound and the separation of a mixture of isomers into the single isomers may be carried out by conventional methods. For example the separation of a mixture of geometric isomers, e.g. cis- and trans-isomers, may be carried out by fractional crystallization from a suitable solvent or by chromatography, either column chromatography or high pressure liquid chromatography. The compounds of formula (II) may be obtained according to known methods from compounds of formula (III)

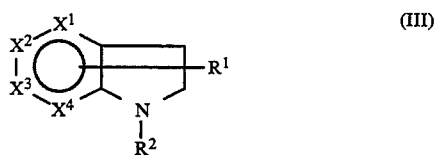

wherein the groups $X^1$ to $X^4$ $R^1$ and $R^2$ are as defined above.

For example the 3-formylazaindole derivative of formula (II) can be obtained from a compound of formula (III) by formylation with N-methyl-formanilide or DMF and phosphorous oxychloride according to the well known Vilsmeyer-Haack method (for a review see W. G. Jackson et al., J. Am. Chem. Soc. 103, 533, 1981). The 2-formylazaindole derivatives are obtained when the 3-position is occupied.

The compounds of formula (III) are known or may be obtained by known methods from known compounds. For example according to R. R. Lorenz et al. (J. Org. Chem. 30, 2531, 1965) the various parent azaindoles (IIIA) may be obtained following the 3-step process herebelow depicted, starting from the appropriate aminomethylpyridine (IV) via the formimidates (V) and the formamidines (VI).

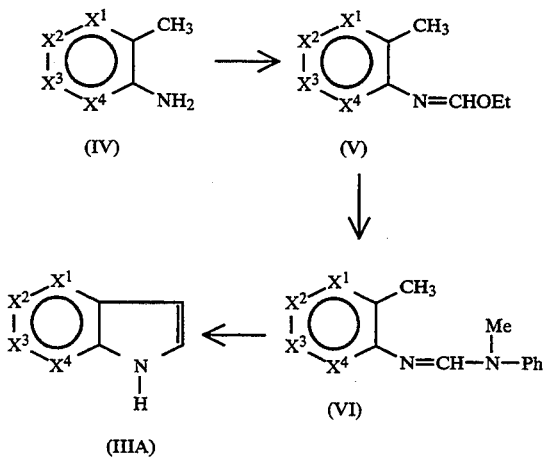

Thus 7-azaindole (IIIA, $X^4$=N, $X^1$=$X^2$=$X^3$=CH) is obtained from 2-amino-3-methylpyridine (IV, $X^4$=N, $X^1$=$X^2$=$X^3$=CH) whilst 4amino-3-methylpyridine (IV, $X^2$=N, $X^1$=$X^3$=$X^4$=CH) gives rise to 5-azaindole (IIIA, $X^2$=N, $X^1$=$X^3$=$X^4$=CH). The 4-azaindole (IIIA, $X^1$=N, $X^2$=$X^3$=$X^4$=CH) is obtained from 3-amino-2-methylpyridine (IV, $X^1$=N, $X^2$=$X^3$=$X^4$=CH).

The compounds of formula (a'), (b'), (c'), (d') and (e') are known or may be obtained by known methods from known compounds.

When in the new compounds of the present invention and in the intermediate products used for their preparation groups are present, which need to be protected before submitting them to the hereabove illustrated reactions, they may be protected before the reaction takes place and then deprotected at the end of the reaction, according to well known methods in organic chemistry.

Pharmacology

The compounds of the invention possess specific tyrosine kinase inhibiting activity. It is believed that tyrosine kinase inhibitors may be of great importance in the control of uncontrolled cellular reproduction, i.e., in cellular reproduction disorders. Hence the compounds according to the present invention can be useful in the treatment of pathological proliferation disorders in mammals, including humans. Typical examples of such disorders are tumors, including leukemia, and psoriasis. They can also be useful in inhibiting the development of the atheromatous plaque. Furthermore, the compounds of the invention have been found to be active as angiogenesis inhibitors.

An angiogenesis inhibitor is an agent capable of suppressing the growth of new blood vessels. Therefore, the compounds of the present invention are useful in treating several pathological conditions in mammals, including humans, where the growth of new blood vessels is detrimental, for example in chronic inflammation, diabetic retinopathy, psoriasis, rheumatoid arthritis, tumor growth, in particular solid tumors and development of metastases.

Besides, the compounds of the invention possess immunomodulating activity and in particular can be used in mammals, including humans, as immunosuppressive agents for the prevention and treatment of rejection phenomena associated with tissue and organ transplantations, graft-versus-host diseases and autoimmune diseases. Recent studies on the molecular basis of neoplastic transformation have identified a family of genes, designed oncogenes, whose aberrant expression causes tumorigenesis.

For example, the RNA tumor viruses possess such an oncogene sequence whose expression determines neoplastic conversion of infected cells. Several of their oncogene-encoded proteins, such as $pp60^{v\text{-}src}$, $p70^{gag\text{-}yes}$, $p130^{gag\text{-}fps}$ and $P70^{gag\text{-}fgr}$ display protein tyrosine kinase activity, that is they catalyse the transfer of the $\gamma$-phosphate from adenosine triphosphate (ATP) to tyrosine residues in protein substrate. In normal cells, several growth factor receptors, for example the receptors for PDGF, EGF, $\alpha$-TGF and insulin, display tyrosine kinase activity.

Binding of the growth factor (GF) activates the receptor tyrosine kinase to undergo autophosphorylation and to phosphorylate closely adjacent molecules on tyrosine. Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyrosine kinases that are either overproduced and/or display altered substrate specificity may cause loss of growth control and/or neoplastic transformation. Accordingly, a specific inhibitor of tyrosine kinase can be useful in investigating the mechanism of carcinogenesis, cell proliferation and differentiations and it can be effective in prevention and chemotherapy of cancer and in other pathological proliferative conditions, for instance as mentioned above. The tyrosine specific protein kinase activity of these compounds is shown, e.g., by the fact that they are active in the in vitro test described herebelow.

Tyrosine kinase purification.

The enzyme used in our test was the p45 v-abl tyrosine kinase which represents the catalytic domain of the Abelson tyrosine kinase (isolated from the Abelson murine leukemia virus). The p45 v-abl kinase was produced and isolated as described by Wang et al. in J. Biol. Chem. 260, 64 (1985) and by Ferguson et al. in J. Biol. Chem. 260, 3652 (1985) and in Biochem. J. 257, 321 (1989).

Exogenous Substrate Kinase Assay.

($Val^5$)-Angiotensin II phosphorylation was performed by incubation with 40 ng of purified abl-kinase and ($\gamma$-$^{32}$P)-ATP, in 50 $\mu$l of buffer containing Tris-HCl 25 mM, pH 8.0, $MgCl_2$ 10 mM and dithiothreitol 0.1 mM (kinase buffer). The reaction mixture was incubated for the indicated time at 30° C. and the reaction stopped by adding 50 $\mu$l of 5% trichloroacetic acid.

After a brief incubation on ice, tubes were centrifuged. The supernatants were spotted on phosphocellulose paper squares (Whatman P-81) and washed extensively in acetic acid. The radioactivity bound to dried phosphocellulose squares was measured in a liquid scintillation counter. $IC_{50}$ values were calculated from triplicate determinations of each experimental point. Each inhibitor was tested at concentrations ranging from 0 to 400 $\mu$g in the presence of fixed concentrations of peptide (2 mM) and ATP (50 $\mu$M).

The activity data of two representative compounds of the present invention are set out in Table 1.

TABLE 1

| p45 v-abl kinase inhibition | $IC_{50}(\mu m)$ |
| --- | --- |
| 3-[(7-azaindol-3-yl)methylen]-2-oxindole | 0.05 |
| 2-cyano-3-(7-azaindol-3-yl)acrylamide | 4.7 |

In view of their high activity and low toxicity, the compounds of the invention can be used safely in medicine. For example, the approximate acute toxicity ($LD_{50}$) of the compounds of the invention in the mouse, determined by single administration of increasing doses and measured on the seventh day after the treatment, was found to be negligible.

The compounds of the invention can be administered in a variety of dosage forms, e.g. orally, in the form of tablets, capsules, sugar- or film-coated tablets, liquid solutions or suspensions; rectally, in the form of suppositories; parenterally, e.g. intramuscularly, or by intravenous injection or infusion; or topically. The dosage depends on the age, weight, condition of the patient and administration route; for example, the dosage adopted for oral administration to adult humans may range from about 10 to about 150-200 mg per dose, from 1 to 5 times daily. Of course, these dosage regimens may be adjusted to provide the optimal therapeutic response.

The invention includes pharmaceutical compositions comprising a compound of formula (I) or a pharmaceutically acceptable salt thereof in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating or film-coating processes.

The liquid dispersion for oral administration may be e.g., syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g., sterile water, olive oil, ethyl oleate, glycols, e.g., propylene glycol, and, if desired, a suitable amount of lidocaine hydrochloride.

The solutions for intravenous injections or infusion may contain as carrier, for example, sterile water or, preferably, they may be in the form of sterile, aqueous, isotonic saline solutions.

The suppositories may contain, together with the active compound, a pharmaceutically acceptable carrier, e.g., cocoa-butter, polyethylene glycol, a polyoxyethylene sorbitan fatty acid ester surfactant or lecithin. Compositions for topical application, e.g., creams, lotions, or pastes, can be prepared by admixing the active ingredient with a conventional oleaginous or emulsifying excipient.

A further object of the present invention is a combined method of treatment of cancer in mammals, including humans, in need of such treatment, said method comprising administering 1) a compound of formula (I), or a pharmaceutically acceptable salt thereof, and
2) an additional antitumor agent, in amounts, and close enough together in time sufficient to produce a therapeutically useful effect.

Object of the present invention is also to provide products containing a compound of formula (I), or a pharmaceutically acceptable salt, and an additional antitumor agent as a combined preparation for simultaneous, separate or sequential use in anti-cancer therapy.

The term "antitumor agent" is meant to comprise both a single antitumor drug and "cocktails", i.e. a mixture of such drugs, according to the clinical practice.

Antitumor agents that can be formulated with a compound of the invention or, alternatively, can be administered in a combined method of treatment, are, e.g., doxorubicin, daunomycin, epirubicin, idarubicin, etoposide, fluorouracil, mephalan, cyclophosphamide, bleomycin, vinblastin and mitomycin or a mixture of two or more thereof.

The compounds of the invention can therefore be used in a treatment to ameliorate a cancer pathology. They may be administered to a patient suffering from a cancer treatable with an antitumor agent, for example an anthracycline glycoside such as doxorubicin, daunomycin, epirubicin or idarubicin as mentioned above, together with the antitumor agent.

A compound of the invention and an antitumor agent such as, e.g., an anthracycline glycoside can be administered to improve the condition of a patient having, e.g., a leukaemia such as myeloblastic leukaemia, lymphoma, sarcoma, neuroblastoma. Wilm's tumor or malignant neoplasm of the bladder, breast, lung or thyroid. The following examples illustrate but do not limit the invention:

EXAMPLE 1

(Z)-3-[(7-azaindol-3-yl)methylen]-2-oxindole (I, $X^4$=N, $X^1$=$X^2$=$X^3$=CH, R=e, $R^1$=$R^2$=$R^3$=H)

A solution of 3-formyl-7-azaindole (1.46 g, 0.010 mol) 2-oxindole (1.332 g, 0.010 mol) and piperidine (0.255 g, 0.003 mol) in absolute ethanol (50 ml) is heated for 3 h at reflux. The reaction mixture is chilled to room temperature, the precipitate filtered, the residue washed with ice-cooled ethanol and dried under vacuum. Almost pure title compound is so obtained in 81% yield (2.126 g).

Compounds of higher purity are obtained by crystallization from ethanol. m.p. >280° C. $C_{16}H_{11}N_3O$ requires : C 73.55 H 4.24 N 16.08 found : C 73.33 H 4.29 N 16.05 MS m/z : 261. NMR δppm (DMSO): 6.84 (1H,d,J=7.6 Hz), 6.99 (1H,t,J=7.6 Hz), 7.15 (1H,t,J=7.6 Hz), 7.27 (1H,dd,J=4.7, 8.0 Hz), 7.87 (1H,d,J=7.6 Hz), 8.13 (1H,S), 8.33 (1H,dd,J=1.5, 4.7 Hz), 8.60 (1H,dd,J=1, 5, 8.0 Hz), 9.50 (1H,S), 10.57 (1H,bs), 12.5 (1H,bs).

According to the above described procedure and starting from the appropriate compounds of formula (II) and of formulae (a'), (b'), (c'), (d') and (e'), respectively one can prepare the following compounds as single E- or Z-isomers, as well as their E,Z-mixtures: 2-cyano-3-(7-azaindol-3-yl)acrylamide.

MS m/z : 212. NMR δppm (DMSO): 7.30 (1H,dd,J=4.9, 7.8 Hz), 7.55, 7.80 (two bs, 2H), 8.35-8.50 (4H,m), 12.9 (1H,bs);
2-cyano-3-(7-azaindol-3-yl)acrylanilide;
2-cyano-3-(7-azaindol-3-yl)thioacrylamide;
2-cyano-3-(7-azaindol-3-yl)acrylonitrile;
5-hydroxy-3-[(7-azaindol-3-yl)methylen]-2-oxindole;
2-cyano-3-(6-azaindol-3-yl)acrylamide;
2-cyano-3-(6-azaindol-3-yl)acrylanilide;
2-cyano-3-(6-azaindol-3-yl)thioacrylamide;
2-cyano-3-(6-azaindol-3-yl)acrylonitrile;
3-[(6-azaindol-3-yl)methylen]-2-oxindole;
5-hydroxy-[(6-azaindol-3-yl)methylen]-2-oxindole;
2-cyano-3-(5-azaindol-3-yl)acrylamide;
2-cyano-3-(5-azaindol-3-yl)acrylanilide;
2-cyano-3-(5-azaindol-3-yl)thioacrylamide;
2-cyano-3-(5-azaindol-3-yl)acrylonitrile; 3-[(5-azaindol-3-yl)methylen]-2-oxindole;
5-hydroxy-3-[5-azaindol-3-yl]-2-oxindole;
2-cyano-3-(4-azaindol-3-yl)acrylamide;
2-cyano-3-(4-azaindol-3-yl)acrylanilide;
2-cyano-3-(4-azaindol-3-yl)thioacrylamide;
2-cyano-3-(4-azaindol-3-yl)acrylonitrile; 3-[(4-azaindol-3-yl)methylen]-2-oxindole; and
5-hydroxy-3-[(4-azaindol-3-yl)methylen]-2-oxindole.

EXAMPLE 2

5-Hydroxy-3-[(7-azaindol-3-yl)methylen]-2-oxindole (I, $X^4$=N, $X^1$=$X^2$=$X^3$=CH, R=e, $R^1$=$R^2$=H, $R^3$=5-OH)

To a stirred solution of 5-methoxy-3-[(7-azaindol-3yl)methylen]-2-oxindole (2.91 g, 0.010 mol) in anhydrous dichloromethane (100 ml) is added at −78° C. under nitrogen, over a period of 20 min, a 1M solution of boron tribromide in dichloromethane (30 ml, 0.030 mol). The resulting mixture is stirred for another 1 h at −78° C. and then allowed to warm up to r.t. After stirring for 1.5 h at r.t. the mixture is cooled to −10° C. and then quenched by dropwise addition of water (100 ml) over a 10-min period. After addition of ethyl acetate (100 ml) the organic layer is separated, washed with water, dried over $Na_2SO_4$ and evaporated under vacuum to dryness. The residue is crystallized from ethanol thus giving pure title compound in 70% yield (1.94 g). $C_{16}H_{11}N_3O_2$ requires : C 69.31 H 4.00 N 15.15 found: C 69.15 H 4.10 N 15.05 MS m/z : 277.

Following the above described procedure and starting from a phenolic methyl ether of formula (I), which, e.g., may be obtained according to the procedure described in example 1, the corresponding phenolic compound of formula (I) may be obtained.

EXAMPLE 3

5-Amino-3-[(7-azaindol-3-yl)methylen]-2-oxindole (I, $X^4$=N, $X^1$=$X^2$=$X^3$=CH, R=e, $R^1$=$R^2$=H, $R^3$=5-$NH_2$)

To a solution of 5-nitro-3-[(7-azaindol-3-yl)methylen]2-oxindole (3.06 g, 0.010 mol) in anhydrous ethanol (200 ml) is added palladium on charcoal (100 mg) and the mixture is hydrogenated at r.t. and atmospheric pressure until 3 equivalent of hydrogen has been taken up. The hydrogen uptake is graphed as a function of time. The catalyst is filtered and the solution concentrated under vacuum until crystallization begins. Then the mixture is cooled to 0°-5° C., filtered, the residue washed with ice-cooled ethanol and dried under vacuum.

Thus almost pure 'title compound is obtained in 80% yield (2.21 g).

$C_{16}H_{12}N_4O$ requires : C 69.55 H 4.38 N 20.28 found : C 69.47 H 4.25 N 20.30 MS m/z : 276.

Proceeding analogously and starting from a nitro compound of formula (I), which, e.g., may be obtained according to the procedure described in Example 1, the corresponding amino compound of formula (I) can be obtained.

EXAMPLE 4

(Z)-3-[(1-methyl-7-azaindol-3-yl)methylen]-2-oxindole (I, $X^4$=N, $X^1$=$X^2$=$X^3$=CH, R=e, $R^1$=$R^3$=H, $R^2$=$CH_3$)

To a suspension of 95% sodium hydride (0.280 g, 0.011 mol) in DMF (100 ml) cooled with an ice-n-propanol bath is added over 15 min with stirring a solution of (Z)-3-[(7-azaindol-3-yl)methylen]-2-oxindole (2.61 g, 0.010 mol) in DMF (50 ml). When the evolution of hydrogen stopped, a solution of iodomethane (1.56 g, 0.011 mol) in DMF (50 ml) is added over 15 min and the mixture is stirred at r.t. for 3 h. Most of the DMF is distilled off in vacuo, water is then added to the residue and the product extracted into ethyl acetate. The organic solution containing the desired product is dried ($Na_2SO_4$), the solvent evaporated and the remaining oil is crystallized by trituration with ethanol. Thus pure title compound is obtained in 60% yield. $C_{17}H_{13}N_3O$ requires : C 74.19 H 4.73 N 15.27 found : C 74.05 H 4.55 N 15.05 MS m/z : 275.

By this procedure compounds of formula (I) in which $R^2$ is $C_1-C_6$ alkyl can be prepared from compounds of formula (I) in which $R^2$ is hydrogen.

EXAMPLE 5

(Z)-3-[(1-acetyl-7-azaindol-3-yl)methylen]-2-oxindole (I, $X^4$=N, $X^1$=$X^2$=$X^3$=CH, R=e, $R^1$=$R^3$=H, $R^2$=$COCH_3$).

A mixture of (Z)-3-[(7-azaindol-3-yl)methylen]-2-oxindole (2.61 g, 0.010 mol), potassium acetate (0.98 g, 0.010 mol) and acetic anhydride (10 ml) is heated at reflux temperature for 15 h and then concentrated under vacuum. The residue is taken up with ethyl acetate and water, the organic phase separated, washed with water, dried over $Na_2SO_4$ and evaporated under vacuum. The residue is crystallized from ethanol to give pure title compound in 65% yield.

$C_{18}H_{13}N_3O_2$ requires : C 71.28 H 4.32 N 13.85 found : C 71.15 H 4.25 N 13.65 MS m/z : 303

By this procedure compounds of formula (I) in which $R^2$ is acetyl can be prepared from compounds of formula (I) wherein $R^2$ is hydrogen.

EXAMPLE 6

3-[(4-dimethylamino-1-methyl-5-azaindol-3-yl)methylen]2-oxidole. (I, $X^2$=N, $X^1$=$X^3$=$X^4$=CH, R=e $R^1$=4-$NMe_2$, $R^2$=Me, $R^3$=H )

A mixture of 3-[(4-chloro-1-methyl-5-azaindol-3-yl)methylen]2-oxindole (3.095 g, 0.010 mol) and dimethylamine (4.51 g, 0.1 mol) is heated at about 150° C. for 20 h in a pressure vessel. The excess of dimethylamine is evaporated under vacuum, the residue taken up in ethyl acetate after alkalinization with sodium hydroxyde solution, the organic layer separated, washed with water, dried and evaporated under vacuum. The residue is chromatographed on a silica gel column using dichloromethane-ethanol mixtures as eluant, thus giving pure title compound.

$C_{19}H_{18}N_4O$ requires : C 71.68 H 5.70 N 17.60 found : C 71.51 H 5.65 N 17.55 MS m/z : 318.

By proceeding analogously compounds of formula (I) wherein $R^1$ is a -$NR^4R^5$ group can be obtained from compounds of formula (I) wherein $R^1$ is chlorine.

EXAMPLE 7

3-[(4-methoxy-1-methyl-5-azaindol-3-yl)methylen]-2oxindole. (I, $X^2$=N, $X^1$=$X^3$=$X^4$=CH, R=e, $R^1$=OMe, $R^2$=Me, $R^3$=H)

A solution of 3-[(4-chloro-1-methyl-5-azaindol-3-yl)methylen]-2-oxindole (3.095 g, 0.010 mol) and potassium methoxide (0.70 g, 0.010 mol) in methanol (50 ml) is heated in a sealed tube for 6 h at about 120° C. The solution is concentrated under vacuum, diluted with water and the product extracted with ethyl acetate. The organic layer is washed, dried and evaporated under vacuum. The residue is submitted to column chromatography on silica gel using dichloromethane-methanol mixtures as eluant. Thus pure title compound is obtained in about 50% yield.

$C_{18}H_{15}N_3O_2$ requires : C 70.81 H 4.95 N 13.76 found : C 70.75 H 4.90 N 13.72 MS m/z : 305.

According to this procedure and starting from a compound of formula (I) wherein $R^1$ is chlorine and using the appropriate potassium $C_1-C_6$ alkoxide one can obtain a compound of formula (I) wherein $R^1$ is $C_1-C_6$ alkoxy.

EXAMPLE 8

7-Azaindole-3-carboxaldeyde. (II, $X^4$=N, $X^1$=$X^2$=$X^3$=CH, $R^1$=$R^2$=H)

A solution of 7-azaindole (23.6 g, 0.20 mol) and hexamethylenetetramine (42 g, 0.30 mol) in 33% acetic acid (84 g, 1.4 mol and 168 ml $H_2O$) is refluxed for 6 h. The resulting clear yellow solution is diluted with water, and the product is allowed to crystallize in the refrigerator overnight. Recrystallization of the crude product from water gave almost pure title compound in 50% yield (14.9 g). m.p. 216°-218° C.

$C_8H_6N_2O$ requires : C 65.74 H 4.13 N 19.17 found : C 65.65 H 4.05 N 19.05 MS m/z : 146.

The isomeric 4-, 5- or 6-azaindole-3-carboxaldehydes can be obtained by the above described procedure starting from the 4-, 5- or 6-azaindoles respectively.

EXAMPLE 9

Tablets each weighing 0.150 g and containing 25 mg of the active substance, can be manufactured as follows: composition (for 10,000 tablets):

| | |
|---|---|
| 3-[(7-azaindol-3-yl)methylen]-2-oxindole | 250 g |
| Lactose | 800 g |
| Corn starch | 415 g |
| Talc powder | 30 g |
| Magnesium stearate | 5 g |

The 3-[(7-azaindol-3-yl)methylen]-2-oxindole, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 10

Capsules, each dosed at 0.200 g and containing 20 mg of the active substance can be prepared. Composition for 500 capsules:

| | |
|---|---|
| 2-cyano-3-(7-azaindol-3-yl)acrylamide | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. An azaindole compound of formula (I)

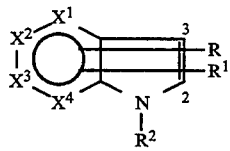 (I)

wherein
one of the groups $X^1$ to $X^4$ is N and the others are CH;
R is a group of formula (a), (b), (c), (d) or (e)

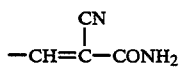 (a)

 (b)

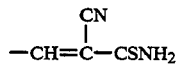 (c)

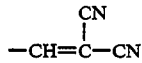 (d)

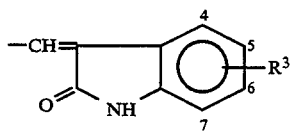 (e)

in which
n is zero or an integer of 1 to 5;
$R^1$ is hydrogen, halogen, $C_1$-$C_6$ alkyl, $C_1$-$C_6$ alkoxy, nitro or a group —$NR^4R^5$, wherein each of $R^4$ and $R^5$ is independently hydrogen or $C_1$-$C_6$ alkyl;
$R^2$ is hydrogen, $C_1$-$C_6$ alkyl, or $C_2$-$C_6$ alkanoyl; $R^3$ is hydrogen, halogen, hydroxy, $C_1$-$C_6$ alkoxy, carboxy, nitro or a group —$NR^4R^5$, wherein $R^4$ and $R^5$ are as defined above, and the pharmaceutically acceptable salts thereof.

2. A compound of formula (I), according to claim 1, wherein:
the groups $X^1$ to $X^4$ are as defined in claim 1;
R is as defined in claim 1 and it is linked in position 2 or 3 of the azaindole ring; n is zero;
$R^1$ is hydrogen, or a halogen or $C_1$-$C_3$ alkoxy group linked to the carbon atom adjacent to the nitrogen atom in the pyridine moiety;
$R^2$ is hydrogen or $C_1$-$C_4$ alkyl; and, when R is group (e),
$R^3$ is hydrogen or a hydroxy group linked in position 5 of the oxindole ring, and the pharmaceutically acceptable salts thereof.

3. A compound selected from a group consisting of the following compounds, which, when appropriate, may be either Z- or E-diastereomers or Z,E-mixtures of said diastereomers:
2-cyano-3-(7-azaindol-3-yl)acrylamide;
2-cyano-3-(7-azaindol-3-yl)acrylanilide;
2-cyano-3-(7-azaindol-3-yl)thioacrylamide;
2-cyano-3-(7-azaindol-3-yl)acrylonitrile;
3-[(7-azaindol-3-yl)methylen]-2-oxindole;
5-hydroxy-3-[(7-azaindol-3-yl)methylen]-2-oxindole;
2-cyano-3-(6-azaindol-3-yl)acrylamide;
2-cyano-3-(6-azaindol-3-yl)acrylanilide;
2-cyano-3-(6-azaindol-3-yl)thioacrylamide;
2-cyano-3-(6-azaindol-3-yl)acrylonitrile;
3-[(6-azaindol-3-yl)methylen]-2-oxindole;
5-hydroxy-[(6-azaindol-3-yl)methylen]-2-oxindole;
2-cyano-3-(5-azaindol-3-yl)acrylamide;
2-cyano-3-(5-azaindol-3-yl)acrylanilide;
2-cyano-3-(5-azaindol-3-yl)thioacrylamide;
2-cyano-3-(5-azaindol-3-yl)acrylonitrile;
3-[(5-azaindol-3-yl)methylen]-2-oxindole;
5-hydroxy-3-[5-azaindol-3-yl]-2-oxindole;
2-cyano-3-(4-azaindol-3-yl)acrylamide;
2-cyano-3-(4-azaindol-3-yl)acrylanilide;
2-cyano-3-(4-azaindol-3-yl)thioacrylamide;
2-cyano-3-(4-azaindol-3-yl)acrylonitrile;
3-[(4-azaindol-3-yl)methylen]-2-oxindole;
5-hydroxy-3-[(4-azaindol-3-yl)methylen]-2-oxindole;
and, if the case, the pharmaceutically acceptable salts thereof.

4. A pharmaceutical composition containing a suitable carrier and/or diluent and, as an active principle, a compound of formula (I) according to claim 1 or a pharmaceutically acceptable salt thereof.

5. A method for producing tyrosine kinase inhibition in a patient in need of it, said method comprising administrering to said patient an effective amount of a compound of formula (I), according to claim 1, or a pharmaceutically acceptable salt thereof.

6. A method for producing an antiproliferative effect in a patient in need of it, said method comprising administrering to the said patient an effective amount of a compound of formula (I), according to claim 1, or a pharmaceutically acceptable salt thereof.

7. A method for producing an anti-cancer effect or treating coronary artery disease or controlling angiogenesis in a patient in need of it, said method comprising administering to the said patient an effective amount of a compound of formula (I), according to claim 1, or a pharmaceutically acceptable salt thereof.

8. Product containing a compound of formula (I), according to claim 1, or a pharmaceutically acceptable salt thereof, and an anti-tumor agent as a combined preparation for simultaneous, separate or sequential use in anti-cancer theraphy.

* * * * *

UNITED STATES PATENT AND TRADEMARK OFFICE
CERTIFICATE OF CORRECTION

PATENT NO. : 5,397,787
DATED : March 14, 1995
INVENTOR(S) : Franco Buzzetti et al It is certified that error appears in the above-indentified patent and that said Letters Patent is hereby corrected as shown below:

Column 3, line 10, delete "[5-azaindol-3yl] and insert therefor --[(5-azaindol-3yl)methylen]--.

Column 5, line 5, formula III should be as follows:

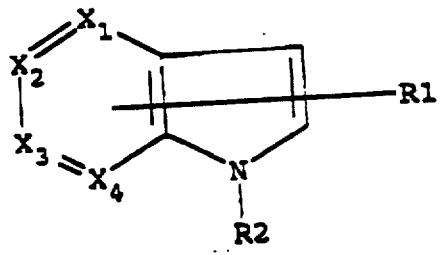

Column 14, line 22, delete "[5-azaindol-3yl] and insert therefor --[(5-azaindol-3yl)methylen]--.

Signed and Sealed this

Seventeenth Day of October, 1995

Attest:

BRUCE LEHMAN

Attesting Officer

Commissioner of Patents and Trademarks